(12) United States Patent
Kotovsky et al.

(10) Patent No.: US 8,342,005 B2
(45) Date of Patent: Jan. 1, 2013

(54) MICRO-OPTICAL-MECHANICAL SYSTEM PHOTOACOUSTIC SPECTROMETER

(75) Inventors: Jack Kotovsky, Oakland, CA (US); William J. Benett, Livermore, CA (US); Angela C. Tooker, Dublin, CA (US); Jennifer B. Alameda, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 517 days.

(21) Appl. No.: 12/628,952

(22) Filed: Dec. 1, 2009

(65) Prior Publication Data
US 2010/0139368 A1 Jun. 10, 2010

Related U.S. Application Data

(60) Provisional application No. 61/118,966, filed on Dec. 1, 2008.

(51) Int. Cl.
G01N 21/00 (2006.01)
(52) U.S. Cl. .................... 73/24.02; 73/24.01; 73/570
(58) Field of Classification Search .................. 73/24.01, 73/24.02, 570
See application file for complete search history.

(56) References Cited

U.S. PATENT DOCUMENTS

| | | | |
|---|---|---|---|
| 4,545,253 A * | 10/1985 | Avicola | 73/655 |
| 7,909,768 B1 * | 3/2011 | Turcott | 600/481 |
| 2002/0063866 A1 * | 5/2002 | Kersey et al. | 356/478 |
| 2002/0171815 A1 * | 11/2002 | Matsuyama et al. | 355/55 |
| 2008/0297772 A1 * | 12/2008 | Rogers et al. | 356/73.1 |
| 2009/0234337 A1 * | 9/2009 | Ely et al. | 606/9 |
| 2009/0234338 A1 * | 9/2009 | Roth et al. | 606/9 |
| 2009/0234340 A1 * | 9/2009 | Behrakis | 606/9 |
| 2009/0234341 A1 * | 9/2009 | Roth | 606/9 |
| 2009/0234342 A1 * | 9/2009 | Ely et al. | 606/9 |
| 2009/0234343 A1 * | 9/2009 | Behrakis | 606/9 |

* cited by examiner

*Primary Examiner* — David A. Rogers
*Assistant Examiner* — Rodney T Frank
(74) *Attorney, Agent, or Firm* — John P. Wooldridge

(57) ABSTRACT

All-optical photoacoustic spectrometer sensing systems (PASS system) and methods include all the hardware needed to analyze the presence of a large variety of materials (solid, liquid and gas). Some of the all-optical PASS systems require only two optical-fibers to communicate with the opto-electronic power and readout systems that exist outside of the material environment. Methods for improving the signal-to-noise are provided and enable mirco-scale systems and methods for operating such systems.

47 Claims, 4 Drawing Sheets

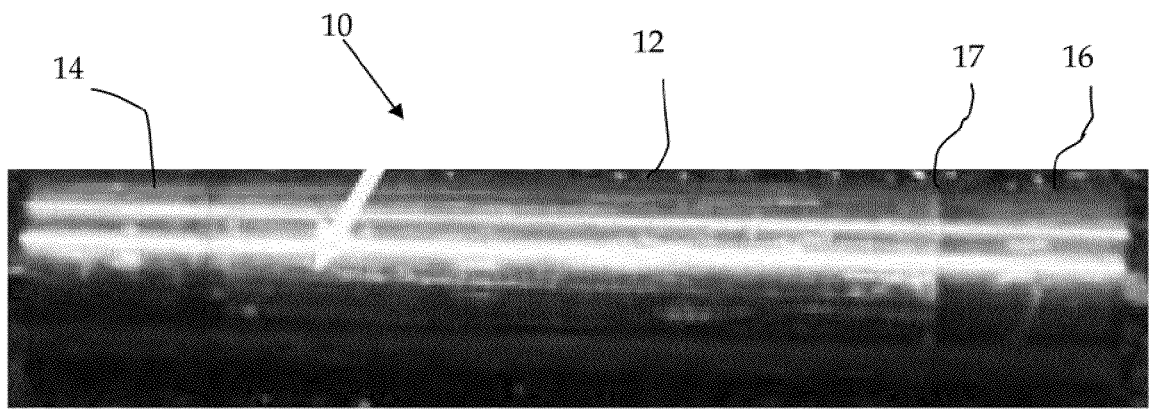
Figure 1A
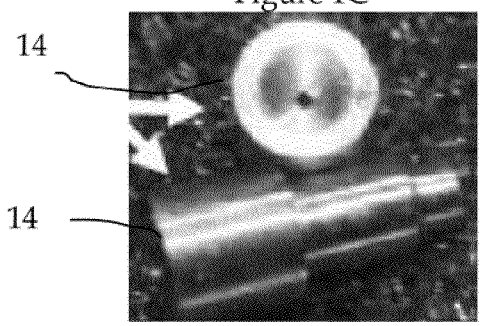
Figure 1C
Figure 1B

Figure 1D
Figure 1E
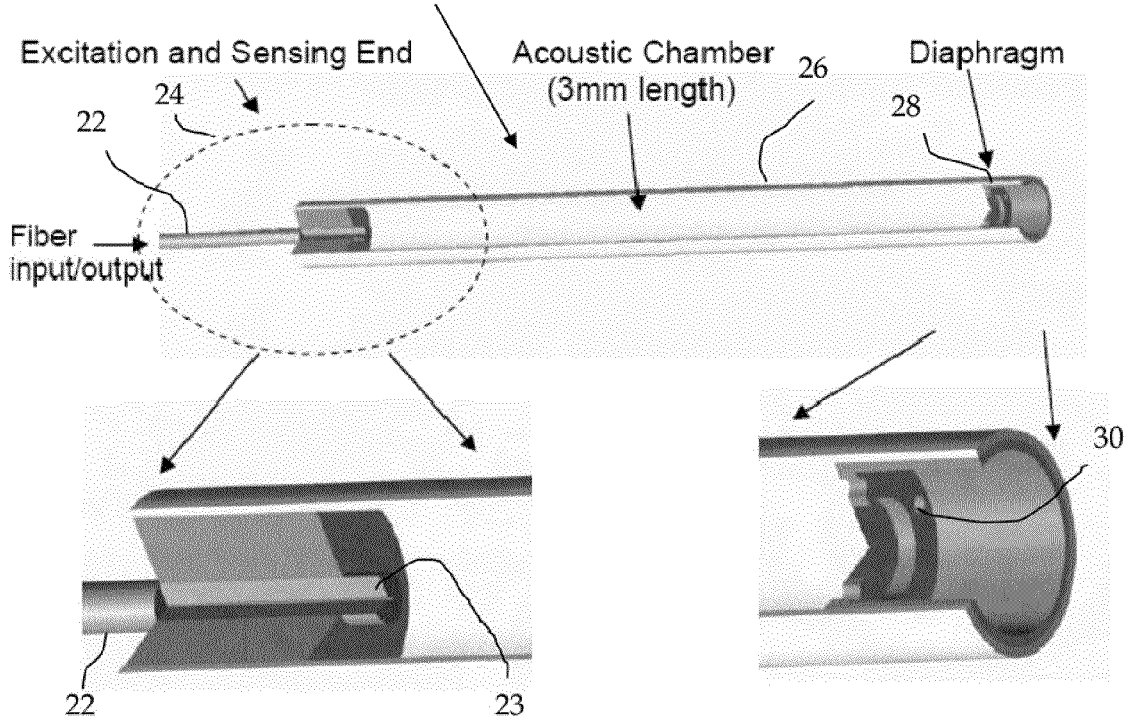
Figure 2A
Figure 2B
Figure 2C

MICRO-OPTICAL-MECHANICAL SYSTEM PHOTOACOUSTIC SPECTROMETER

This application claims priority to U.S. Provisional No. 61/118,966, filed Dec. 1, 2008.

The United States Government has rights in this invention pursuant to Contract No. DE-AC52-07NA27344 between the United States Department of Energy and Lawrence Livermore National Security, LLC.

BACKGROUND OF THE INVENTION

1. Field of the Invention

The present invention relates to spectrometry, and more specifically, it relates to solid, liquid and gas sensors.

2. Description of Related Art

A variety of different molecules (solid, liquid and gas) can absorb energy at specific wavelengths of light. The resulting energy increase by the optically excited gas molecules may dissipate via collisions between the excited molecules and the surrounding molecules present, ultimately transferring the energy from vibration to translation. If the optical excitation source is pulsed, this results in periodic local heating the molecules, which induces a pressure change. The pressure change induces an acoustic wave which can be detected using a microphone. As different molecules absorb energy at different wavelengths, optically scanning a variety of different wavelengths allows identification of the molecules present based on the wavelengths at which an acoustic wave is detected. This technique has been used in large scale sensing apparatuses; however, a successful sensor fabricated on a micro-scale has not been achieved.

SUMMARY OF THE INVENTION

It is an object of the present invention to provide micro-scale gas sensors capable of analyzing small samples and detecting a variety of different material with rapid non-invasive measurements.

Another object is to provide micro-scale sensors that include means for removing signal artifacts.

These and other objects will be apparent based on the disclosure herein.

Photoacoustic Spectroscopy (PAS) is a versatile tool that allows trace material sensing. By providing a pulsed optical input (at a wavelength absorbed by a material to be detected) a pressure/acoustic wave is induced which can then be measured via a pressure transducer such as a microphone or a thin, flexible member such as a diaphragm and a cantilevered beam. Embodiments of the present invention can comprise 4 distinct elements: 1) an acoustic chamber having a material (gas) access port, 2) a laser input fiber ferrule (fiber connector), 3) a sensing fiber ferrule and 4) a micro-optical-mechanical system (MOMS) sensor. Separate fibers are attached to the two ferrules. One fiber carries pulsed laser excitation that induces acoustic waves in the acoustic chamber and the second fiber detects the deflection of the MOMS sensor in response to the acoustic wave.

The MOMS sensor is a micro-fabricated device of, e.g., silicon, that may be less than 1 mm in diameter, which contains an acoustic detector (e.g., a diaphragm or a cantilevered beam) at its center which deflects in proportion to an applied acoustic wave. Modifying the diameter and thickness of the acoustic detector controls the sensitivity of the sensor. Uses include small volume gas sensing, material aging and stockpile stewardship. Gas sensing and spectrometers are in regular use in many commercial applications. This invention offers, e.g., a very small, inexpensive and all optical (not sensitive to electrical noise and inherently safe) solution.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 1A shows an assembled prototype of the present photo-acoustic spectrometer.

FIG. 1B shows a side view of the laser input fiber ferrule.

FIG. 1C shows an end view of laser input fiber ferrule.

FIG. 1D shows a MOMS optical sensor.

FIG. 1E shows an end view of the sensing fiber ferrule.

FIG. 2A shows a cut-away view of a photo-acoustic spectrometer.

FIG. 2B shows an enlarged view of the excitation and sensing end of FIG. 2A.

FIG. 2C shows an enlarged view of the end of acoustic chamber and the diaphragm of FIG. 2A.

DETAILED DESCRIPTION OF THE INVENTION

Figure 3A:
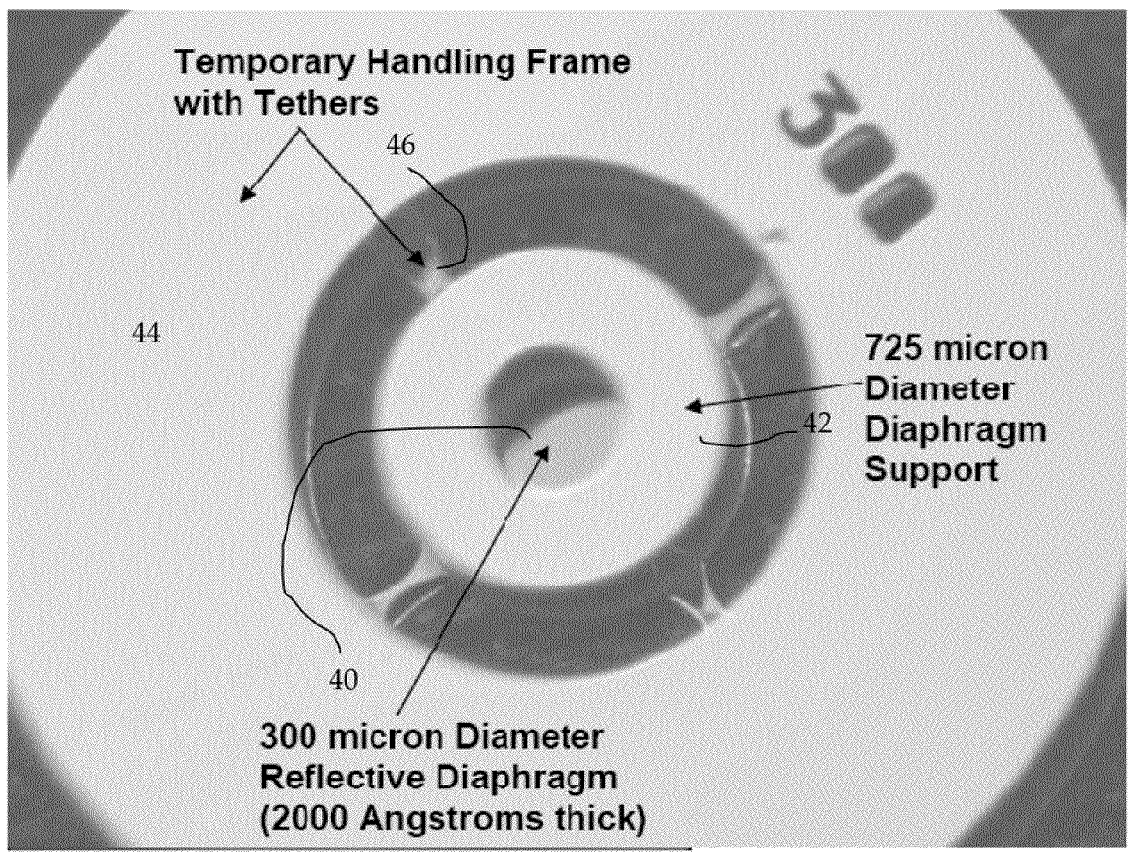
FIG. 3A shows a picture of a MOMS sensor.
Figure 3B:
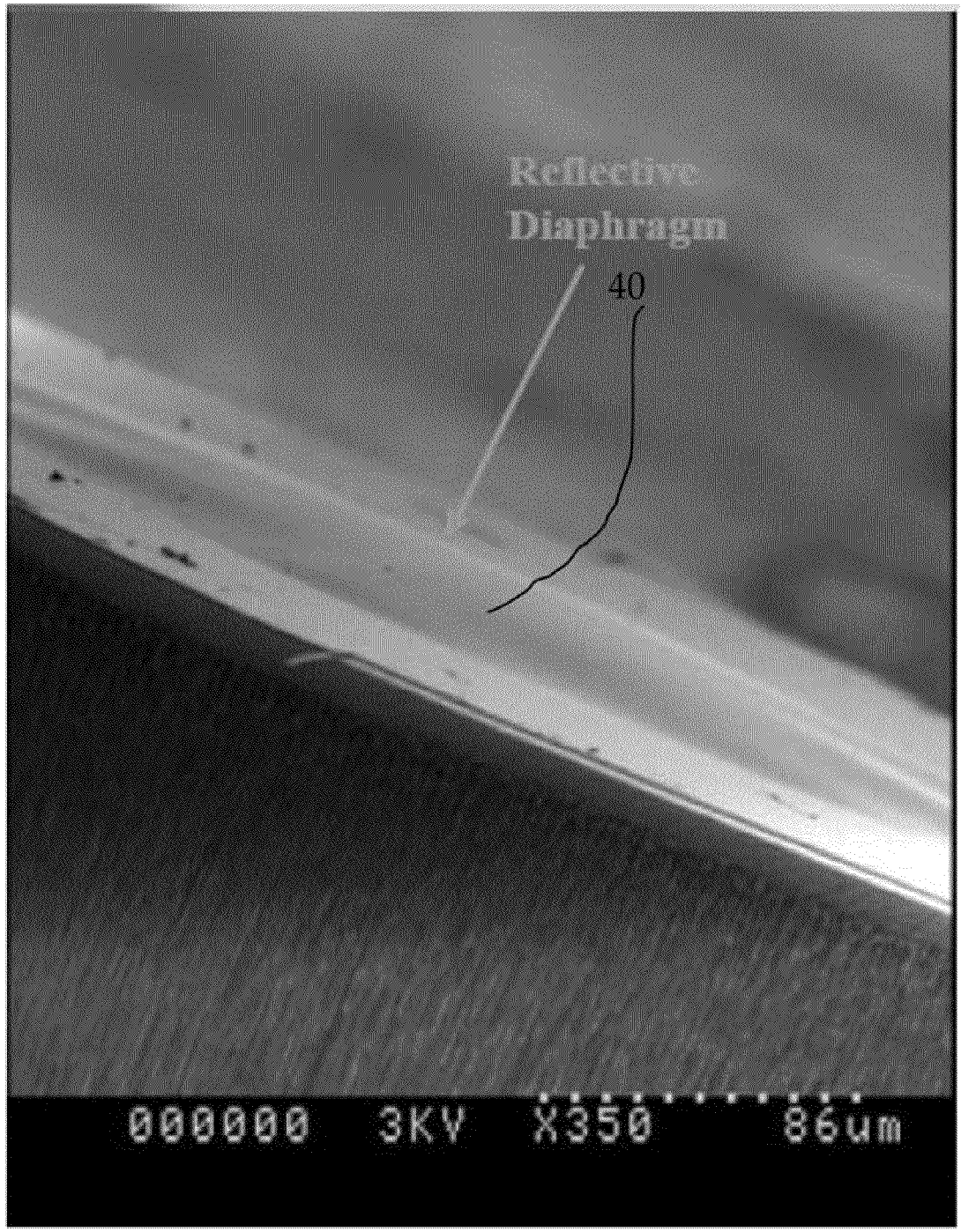
FIG. 3B shows a scanning electron micrograph of the diaphragm of FIG. 3A.

FIG. 1A shows an assembled prototype 10 of an embodiment of the present photo-acoustic spectrometer which includes an acoustic chamber 12, a laser input fiber ferrule 14, a sensing fiber ferrule 16, and the location 17 of a MOMS optical sensor, also referred to herein as a diaphragm or a flexible membrane 18, which is shown in FIG. 1D as well as FIGS. 3A and 3B. FIG. 1B shows a side view of laser input fiber ferrule 14. FIG. 1C shows an end view of laser input fiber ferrule 14. FIG. 1E shows an end view of the sensing fiber ferrule 16. FIG. 2A shows a cut-away view of a photo-acoustic spectrometer 20 and includes a laser input fiber ferrule 22 at the excitation and sensing end 24, a 3 mm in length acoustic chamber 26, which is formed from glass capillary tubing in some embodiments, and the diaphragm annulus 28. FIG. 2B shows an enlarged view of the excitation and sensing end 24 of FIG. 2A and further shows fiber optic ferrule 22 with an input fiber optic 23. Although this embodiment shows a single fiber, other embodiments utilize a plurality of fibers. The laser input pulse and the vibration detection can be accomplished in a single fiber. The laser input can be provided by a single fiber and the vibration detection can be accomplished with a second fiber that can be located at the same location as the input fiber, or at a different location, e.g., on the opposite side of the flexible member as the input fiber. FIG. 2C shows an enlarged view of the end of acoustic chamber 26 and the diaphragm annulus 28 of FIG. 2A and further shows a gas inlet port 30. Diaphragm annulus 28 is formed of silicon in this embodiment and supports and provides tension to the diaphragm, which is also referred to as a flexible membrane in some embodiments. In some embodiments, the diaphragm is about 0.2 μm thick.

In some embodiments, the laser input fiber ferrule is attached at one end of the acoustic chamber and the sensing fiber ferrule is attached at the opposite end. A fiber is inserted into the laser input fiber ferrule and then inserted into one end of the acoustic chamber. This fiber carries the pulsed laser excitation that will induce the pressure changes/acoustic waves on the gases (or other materials of interest) inside the chamber. At the opposite end of the acoustic chamber is the sensing fiber ferrule. In some embodiments, a second fiber is inserted into the sensing fiber ferrule. This assembly is then inserted into the opposite end of the acoustic chamber. The MOMS sensor contains a flexible member (e.g., a diaphragm) that responds to the acoustic waves generated within the chamber. The second fiber detects the deflection of the diaphragm. A variety of techniques can be used to detect the deflection. Some of these techniques include laser vibrometry, interferometry and measurement of photodopler shift. The acoustic chamber contains a gas access port allowing the surrounding gases to flow into the chamber for detection. The sensing and stimulating fiber may also be positioned on the same end of the chamber or at arbitrary points in the chamber (in addition to the opposite ends of the chamber as described above).

The MOMS sensor is a micro-fabricated device that can be fabricated from silicon other materials. FIG. 3A shows a picture of a MOMS sensor including a 300 µm diameter, 2000 angstrom thick, reflective diaphragm 40, a 725 µm diameter diaphragm support 42, and the temporary handling frame 44 with tethers 46. FIG. 3B shows a scanning electron micrograph of the diaphragm 40 of FIG. 3A. The natural deflection of the diaphragm 40 can be observed from the figure. This deflection (and hence the sensitivity of the sensor) can be tuned by altering the diameter and thickness of the diaphragm. MOMS sensors can be fabricated from, e.g., silicon wafers, with thin layers of thermally-grown silicon-oxide, low-stress silicon-nitride, and electron-beam evaporated chrome-gold on top. The reflective diaphragm is at the center of the device and is the sensing portion of the device, as it deflects in response to an applied acoustic wave. The reflective diaphragm (generally about 0.2-0.5 µm thick) is comprised, in this embodiment, only of the thin thermally-grown silicon-oxide, low-stress silicon-nitride, and electron-beam evaporated chrome-gold (the silicon is etched off of the reflective diaphragm). Micro-electrictro-mechanical sensor (MEMS) fabrication methods are generally discussed in U.S. patent application Ser. No. 12/274,253, incorporated herein by reference, which also specifically describes diaphragm and cantilevered beam fabrication techniques. Other flexible diaphragm materials may be used as well.

The thickness of the silicon-oxide and silicon-nitride layers directly affects the stress, and thus the sensitivity, of the diaphragm. The chrome-gold layer increases the reflectivity of the diaphragm, enhancing the sensing capabilities of the sensing fiber. Multiple diaphragm diameters were fabricated (ranging from 100 µm to 425 µm) allowing great sensitivity control for tuning the acoustic chamber. Surrounding the reflective diaphragm is the diaphragm support which is an annulus of silicon (less than 1 mm in diameter) that supports and tensions the reflective diaphragm. Surrounding the diaphragm support is the temporary handling frame (another silicon annulus) that is attached to the diaphragm support with tethers comprised of silicon-oxide, silicon-nitride, and chrome-gold. The temporary handling frame is a much larger annulus of silicon (2.5 mm in diameter) that enables easy handling of the sensor. Once the sensor is in place on the sensing fiber ferrule, the tethers are broken and the temporary handling frame is removed.

A photoacoustic spectrometer sensing system (PASS system) of the present invention can to be placed in a space to measure the level of a material of interest such as a gas. The size and all-optical constraints placed on the PASS system demand a new design and new data analysis hardware and techniques.

To measure the presence of a particular gas in a MOMS fabricated cylinder or gas chamber that includes a flexible membrane, a pulse of light, having a wavelength $\lambda_1$ that is selected so that it will be absorbed by the gas of interest, is directed into the cylinder. When the gas absorbs light, the gas temperature rises, which results in a component of increased pressure within the cylinder. The flexible membrane is deflected by the increased pressure. When $\lambda_1$ is turned off, the gas cools and the deflection resolves by vibration of the membrane. The vibration is detected with the sensing fiber optic. The pressure may also be increased locally creating a sound wave within the gas sensing volume. In either case, the acoustic detector is strategically placed to measure potential pressure transients.

A problem can arise from the above described configuration if the size of the chamber is so small that it is impracticable to prevent the pulse of light from interacting with the boundary of the chamber (e.g., the walls the cylinder). In such cases, the pulse of light can heat up the boundary to add another component of increased pressure. In such cases, the deflection of the membrane can be produced by the combined pressure components. The present invention provides methods for distinguishing the vibration component produced from the heated gas from the vibration component produced from the heated boundary. Without distinguishing between these signals, there would be ambiguity as to the presence of the gas because, e.g., signal from the boundary will be produced even if no gas is present.

To overcome the chamber boundary heating problem, a second pulse of light at a wavelength $\lambda_2$ that is not absorbed by the gas of interest is directed into the cylinder during the time that $\lambda_1$ is off. This keeps the wall temperature constant. Therefore, during the off cycle of $\lambda_1$, only the gas cooling allows the deflected membrane to vibrate. Commercially available laser systems allow fast, continuous control on switching, allowing the duty cycle and the frequency of the switching between the two light sources to be entirely controlled. This allows the system to be run at the natural frequency of the chamber and/or acoustic detector to optimize signal-to-noise of this detection scheme.

If the boundary absorbs the two wavelengths slightly differently, one or both of the wavelengths can be adjusted in power until the noise is minimized to experimentally adjust the system to optimum operating conditions.

The vibration is detectable by, e.g., injecting a white light beam through a beam-splitter, into the same gas volume and onto the membrane. A portion of the white light will be reflected back to a detector and then the light that transmitted through the BS will be reflected by the membrane, at the vibration frequency, back through the BS and to the detection system, which can be, e.g., a quadrature detection system as known in the art, which is briefly discussed below.

The acoustic detection can be accomplished through a variety of means, some of which are described herein, but other means will be understood to those skilled in the art, based on this disclosure. For a remotely addressed, all-optical system (e.g., only accessed by optical fiber), an optical acoustic detector can be created. Several mechanisms can be used to detect diaphragm motion. Examples include commercial solutions like a laser vibrometer, a CW interferometer and a white light interferometric system. The present inventors have used a commercial product made by Fiso Inc., which launches white light into a multimode fiber that can measure Fabry Perot gap changes with great accuracy. The diaphragm surface and the end of the fiber carrying the white light can be positioned and manufactured to create the Fabry Perot cavity. The fiber would look at the face of the diaphragm outside the detection chamber. The stimulus light may or may not be internally reflected within the measurement volume and will not affect the acoustic detection opto-electronics. The optical detection of the diaphragm motion can be accomplished with commercial hardware.

If an all-optical system is not needed, an electronic microphone can be used to detect diaphragm motion. The diaphragm itself can be custom instrumented with piezoresistive traces or capacitive coupling to electronically detect its motion. Exemplary methods of fabrication of diaphragms with piezoresistive traces or capacitive coupling are described in U.S. patent application Ser. No. 12/274,253, titled "Contact Stress Sensor," filed Sep. 10, 2009, incorporated herein by reference.

In some embodiments, a quadrature system is used for signal processing of the detected signal. White light passes through a beamsplitter and is directed onto the membrane. Thus, a portion of the white light (reference) is directed back to the detector. A portion of the light (signal) that is directed onto the membrane will be reflected back through the beamsplitter, into the return fiber and to the detector. At the detector, the reference and signal light interfere and can be interpreted according to methods such a quadrature detection method, as known in the art.

In one case, the chopping is done electronically. One laser is pulsed 180 degrees out of phase with respect to the other laser. In one case, a single laser moves back and forth between two wavelengths or swept continuously through a range of wavelengths. The membrane is designed to vibrate at a specific frequency. The membrane will vibrate at whatever frequency forces it to move. It will move the most if driven at its natural frequency.

In another embodiment, the laser stimulus is chopped with a single wavelength. The gas volume is divided into two areas. One area includes a reference volume with a known gas that is fully captured. The other area is a sampling volume that exchanges with the system under test. Half of the chopped laser stimulus light is directed into one volume and half is directed into the other volume. The diaphragm is heated on either side equally due to absorption of light energy by the diaphragm and walls. If the gas of interest is in the sample volume, that side of the diaphragm will see a pressure change and will displace the diaphragm. The reference volume will contain a gas that does not respond to the laser stimulus (e.g., nitrogen).

The PAS system depends on the measurement of pressure pulses if a gas of interest is present. The sensitivity of this measurement depends on the magnitude of pressure fluctuation around ambient. Although an open-air system is possible, the magnitude is enhanced by an enclosure that constrains the gas volume. Modeling work suggested that a cylindrical acoustic chamber with no significant openings provides excellent pressure response. Modular cylindrical prototypes were designed and fabricated to allow system characterization under varied chamber dimensions. Several chamber lengths and diameters were created.

The present sensor design provides excellent sensitivity and durability. The material choice meets the stringent constraints of weapon systems and survives very long deployments. The present inventors created a variety of optical films. These included combinations of silicon nitride, silicon oxide and metallic coatings. A circular diaphragm was created that includes a multi-layer material stack for stress-tuning. Optical measurements show that an excellent optical return is achieved with a pre-buckled diaphragm. The buckled diaphragm, as exemplified in FIG. 3B, provides enhanced sensitivity by reducing the diaphragm stiffness.

Choice of a specialized optical interferometer readout system allows for very robust diaphragm movement detection. Fiber alignment and positioning of the readout system is not critical, making the overall PAS system very robust. The power and sensing systems are position variable, thus enhancing the long term survivability and simplicity of the system.

In some embodiments, laser power is coupled to the acoustic chamber via the power fiber. It may carry time varying light of a single wavelength with changing power or of two or more wavelengths of light of varied power where the two wavelengths are out of phase with each other in time. The light may also be of constant power in time and varied in wavelength. A single fiber carries the stimulating laser light to the acoustic chamber. The interferometric readout system also uses a single fiber to detect diaphragm motion. This fiber can be coupled to the opposite end of the acoustic chamber. Both coupling ferrules are modular and similar in form to allow efficient testing of varied diaphragm sensors.

The present invention includes methods for detecting a vibration of a flexible member (FM), wherein the FM is operatively fixed relative to an area such that a pressure change in the area will deflect the FM, wherein the area comprises a material of interest (MOI) access port, the method comprising: directing a first pulse of light (FPOL) into the area during a first period of time (FPOT), wherein the FPOL comprises a wavelength $\lambda_1$ that is selected so that it will be absorbed by the MOI, if the MOI is located within the area, and produce first component of increased pressure within the area, wherein the FPOL produced component will produce a first deflection component of the FM, wherein if the FPOL heats a boundary of the area and produces a second component of increased pressure, the second component will produce a second deflection component of the FM; preventing the FPOL from entering the area for a second period of time (SPOT); directing a second pulse of light (SPOL) onto the boundary during the SPOT, wherein the SPOL comprises a wavelength $\lambda_2$ that is selected so that it will heat the boundary to produce a third component of increased pressure within the area that is about equal to the second component of increased pressure, wherein during the SPOT, substantially only the MOI will cool, wherein the first deflection component will at least partially resolve by vibration of the FM; and detecting the vibration. The method can further comprise consecutively repeating the steps of directing a FPOL, preventing the FPOL, directing a SPOL and detecting the vibration. The FM can comprise a reflective surface that is reflective to at least one wavelength of electromagnetic radiation (EMR). The FM can be operatively fixed relative to the area by affixing the FM to the boundary such the FM is a between the area and an external area relative to the area. The FM can be selected from the group consisting of a diaphragm and a cantilevered beam. The diaphragm can comprise a diameter within a range from about 100 μM to about 425 μm. The FM can comprise a thickness within a range from about 0.2 μm to about 0.5 μm. The FM can comprise a flexible membrane. The FM can comprise a micro-optical-mechanical system (MOMS) sensor is a micro-fabricated device. The MOMS sensor can comprise a diameter of about 300 μm diameter and a thickness of about 2000 angstroms. The diaphragm can be pre-buckled. The FM can comprise a diameter and a thickness selected to controls the sensitivity of the FM to pressure. The area can comprise a chamber or a cylinder. The MOI can be selected from the group consisting of a solid, a liquid and a gas. The step of detection can comprise a sensing mechanism selected from the group consisting of laser vibrometry, interferometry and measurement of photodopler shift. The step of detecting the vibration can comprise: directing a first portion of the SPOL through a beam-splitter, then into the area and onto the FM to produce first sensing light; reflecting a second portion of the SPOL to a reflector and then into the area and onto the FM to produce second sensing light; reflecting a portion of the SPOL to a detector; interfering the first sensing light with the second sensing light to produce an interference pattern; and analyzing the pattern with quadrature detection. The step of directing a SPOL can comprise providing the SPOL through a fiber optic having an exit face operatively positioned with respect to the area, wherein the step of detecting the vibration comprises measuring Fabry Perot gap changes between the exit face and the FM. The FPOL and the SPOL can be provided to the area through a single fiber or through separate fiber optics, wherein the separate fiber optics comprise a location selected from the group consisting of at about the same location and at different locations. The FPOL and the SPOL are provided on opposite sides of the FM. The step of detecting the vibration can comprise detecting the vibration with a microphone. The step of detecting the vibration can comprise measuring resistance changes through piezoresistive traces on or in the FM. The step of detecting the vibration can comprise measuring vibration of the FM through capacitive coupling. The method can further comprise substantially equalizing the power level of at least one of the FPOL and the SPOL. The area can be divided into a first area and a second area, wherein the FPOL is directed onto the FM through the first area and the SPOL is directed onto the FM through the second area, wherein the first area comprises the MOI access port, wherein the second area comprises a known material for reference, wherein the known material does not absorb the FPOL. The MOMS sensor can comprise a diameter selected from the group consisting of about 500 μm or less, about 2 mm or less and about 1 cm or less. The area can comprise a long dimension selected from the group consisting of about 100 μm or less and about 20 μm or less.

Other methods can comprise providing a micro-scale gas sensor that includes an acoustic chamber having a gas access port, wherein the acoustic chamber comprises at least one gas inlet port; an input fiber optic ferrule operatively attached to the acoustic chamber such that at least one input fiber optic attached to the input fiber ferrule can direct light into the acoustic chamber; an input fiber optic fixedly attached to the input fiber optic ferrule; a micro-optical-mechanical system (MOMS) sensor comprising a diaphragm, wherein the MOMS sensor is operatively fixed relative to the acoustic chamber such that pressure induced in the chamber will produce a deflection of the flexible membrane, wherein the flexible membrane comprises a reflective surface that is reflective to at least one wavelength of light; a sensing fiber optic ferrule operatively attached to the acoustic chamber such that a sensing fiber optic attached to the sensing fiber ferrule can direct the at least one wavelength onto the flexible membrane; and a sensing fiber optic fixedly attached to the sensing fiber optic ferrule; the method further comprising directing a pulse of excitation light through the input fiber optic and into the acoustic chamber during a first period of time, wherein the pulse of excitation light comprises an wavelength $\lambda_1$ that is selected so that it will be absorbed by a gas of interest and produce a rise in gas of interest temperature that increases pressure within the acoustic chamber which produces a deflection of the flexible membrane; preventing the pulse of excitation light from entering the acoustic chamber for a second period of time, wherein the gas of interest will cool, wherein the deflection will resolve by vibration of the flexible membrane; and detecting the vibration through the sensing fiber. The chamber can comprise an inner surface, wherein when the pulse of excitation light comes in contact with the inner surface, the pulse of excitation light produces a rise in chamber temperature which contributes to the deflection, the method further comprising directing an inner surface heating pulse of light onto the surface during the second time period to keep the chamber from cooling during the second time period, wherein the inner surface heating pulse of light consists essentially of one or more wavelengths $\lambda_2$ that are not absorbed by the gas of interest, whereby only the gas of interest will substantially cool during the second time period.

Embodiments of a sensor according to the present invention can comprise: an acoustic chamber having a gas access port; an input fiber optic ferrule operatively attached to the acoustic chamber such that at least one input fiber optic attached to the input fiber ferrule can direct light into the acoustic chamber; a sensor element comprising an acoustic detector, wherein the sensor element is operatively fixed relative to the acoustic chamber such that pressure induced in the chamber will produce a deflection of the acoustic detector, wherein the acoustic detector comprises a reflective surface that is reflective to at least one wavelength of light; and a sensing fiber optic ferrule operatively attached to the acoustic chamber such that a sensing fiber optic attached to the sensing fiber ferrule can direct the at least one wavelength onto the acoustic detector.

Embodiments of a system for detecting a vibration of a flexible member according to the present invention can comprise: a flexible member (FM) operatively fixed relative to an area such that a pressure change in the area will deflect the FM, wherein the area comprises a material of interest (MOI) access port; means for directing a first pulse of light (FPOL) into the area during a first period of time (FPOT), wherein the FPOL comprises a wavelength $\lambda_1$ that is selected so that it will be absorbed by the MOI, if the MOI is located within the area, and produce first component of increased pressure within the area, wherein the FPOL produced component will produce a first deflection component of the FM, wherein if the FPOL heats a boundary of the area and produces a second component of increased pressure, the second component will produce a second deflection component of the FM; means for preventing the FPOL from entering the area for a second period of time (SPOT); means for directing a second pulse of light (SPOL) onto the boundary during the SPOT, wherein the SPOL comprises a wavelength $\lambda_2$ that is selected so that it will heat the boundary to produce a third component of increased pressure within the area that is about equal to the second component of increased pressure, wherein during the SPOT, substantially only the MOI will cool, wherein the first deflection component will at least partially resolve by vibration of the FM; and means for detecting the vibration. The FM can comprise a reflective surface that is reflective to at least one wavelength of electromagnetic radiation (EMR). The FM can be operatively fixed relative to an area by affixing the FM to the boundary such the FM is a between the area and an external area relative to the area. The FM can be selected from the group consisting of a diaphragm and a cantilevered beam. The diaphragm can comprise a diameter within a range from about 100 μm to about 425 μm. The FM can comprise a thickness within a range from about 0.2 μM to about 0.5 μm. The FM can comprise a flexible membrane. The FM can comprise a micro-optical-mechanical system (MOMS) sensor is a micro-fabricated device. The MOMS sensor can comprise a diameter of about 300 μm diameter and a thickness of about 2000 angstroms. The diaphragm can be pre-buckled. The FM can comprise a diameter and a thickness selected to control the sensitivity of the FM to pressure. The area can comprise a chamber having a long dimension selected from the group consisting of about 100 μm or less and about 20 μm or less and the area can comprises a cylinder. The MOI can be selected from the group consisting of a solid, a liquid and a gas. The means for directing a SPOL can comprise a fiber optic having an exit face operatively positioned with respect to the area and further comprises means for measuring Fabry Perot gap changes between the exit face and the FM. The means for providing a FPOL and the means for providing a SPOL can be selected from the group consisting of a single fiber, separate fiber optics, wherein the separate fiber optics comprise a location selected from the group consisting of at about the same location and at different locations, wherein the different locations are selected from the group consisting of the same side of the FM and opposite sides of the FM. The means for detecting the vibration can comprise a microphone. The FM can comprise piezoresistive traces on or in the FM, wherein the means for detecting the vibration comprise means for measuring resistance changes through the piezoresistive traces. The area can be divided into a first area and a second area, wherein the means for directing the FPOL directs the FPOL onto the FM through the first area and the means for directing the SPOL directs the SPOL onto the FM through the second area, wherein the first area comprises the MOI access port, wherein the second area comprises a known material for reference, wherein the known material does not absorb the FPOL. The MOMS sensor comprises a diameter selected from the group consisting of about 500 µm or less, about 2 mm or less and about 1 cm or less.

U.S. Provisional No. 61/118,966, filed Dec. 1, 2008 is incorporated herein by reference. U.S. patent application Ser. No. 12/274,253, titled "Contact Stress Sensor", filed Sep. 10, 2009 is incorporated herein by reference.

Parkes, A. M., Keen, K. A., McNaghten, E. D., "Trace gas detection using a novel cantilever-based photoacoustic spectrometer with multiplexed optical fiber-coupled diode lasers and fiber-amplification," Fibre Optic Sensors and Applications V, Proc. SPIE, Vol. 67701C, Ed. Eric Udd, 2007. This reference is incorporated herein by reference.

Lindley, R. E., Parkes, A. M., Keen, K. A., McNaghten, E. D., Orr-Ewing, A. J., "A sensitivity comparison of three photoacoustic cells containing a single microphone, a differential dual microphone or a cantilever pressure sensor," Applied Phys. B., Lasers and Optics, 2006. This reference is incorporated herein by reference.

The foregoing description of the invention has been presented for purposes of illustration and description and is not intended to be exhaustive or to limit the invention to the precise form disclosed. Many modifications and variations are possible in light of the above teaching. For example, this present invention is not limited to and all-optical system or method; an electronic acoustic detector is also possible. The acoustic chamber may also be the system itself (i.e., the area of closed volume within an engine) that the sensor is tuned to. This system may be micro or mini scale. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

We claim:

1. A method for detecting a vibration of a flexible member (FM), wherein said FM is operatively fixed relative to an area such that a pressure change in said area will deflect said FM, wherein said area comprises a material of interest (MOI) access port, the method comprising:

directing a first pulse of light (FPOL) into said area during a first period of time (FPOT), wherein said. FPOL comprises a wavelength $\lambda_1$ that is selected so that it will be absorbed by said MOI, if said MOI is located within said area, and produce first component of increased pressure within said area, wherein said FPOL produced component will produce a first deflection component of said FM, wherein if said FPOL heats a boundary of said area and produces a second component of increased pressure, said second component will produce a second deflection component of said FM;

preventing said FPOL from entering said area for a second period of time (SPOT);

directing a second pulse of light (SPOL) onto said boundary during said SPOT, wherein said SPOL comprises a wavelength $\lambda_2$ that is selected so that it will heat said boundary to produce a third component of increased pressure within said area that is about equal to said second component of increased pressure, wherein during said SPOT, substantially only said MOI will cool, wherein said first deflection component will at least partially resolve by vibration of said FM; and detecting said vibration.

2. The method of claim 1, further comprising consecutively repeating the steps of directing a FPOL, preventing said FPOL, directing a SPOL and detecting said vibration.

3. The method of claim 1, wherein said FM comprises a reflective surface that is reflective to at least one wavelength of electromagnetic radiation (EMR).

4. The method of claim 1, wherein said FM is operatively fixed relative to an area by affixing said FM to said boundary such said FM is a between said area and an external area relative to said area.

5. The method of claim 1, wherein said FM is selected from the group consisting of a diaphragm and a cantilevered beam.

6. The method of claim 5, wherein said diaphragm comprises a diameter within a range from about 100 µm to about 425 µm.

7. The method of claim 5, wherein said FM comprises a thickness within a range from about 0.2 µm to about 0.5 µm.

8. The method of claim 1, wherein said FM comprises a flexible membrane.

9. The method of claim 1, wherein said FM comprises a micro-optical-mechanical system (MOMS) sensor is a microfabricated device.

10. The method of claim 9, wherein said MOMS sensor comprises a diameter of about 300 µm diameter and a thickness of about 2000 angstroms.

11. The method of claim 5, wherein said diaphragm is pre-buckled.

12. The method of claim 5, wherein said FM comprises a diameter and a thickness selected to controls the sensitivity of said FM to pressure.

13. The method of claim 1, wherein said area comprises a chamber.

14. The method of claim 13, wherein said area comprises a cylinder.

15. The method of claim 1, wherein said MOI is selected from the group consisting of a solid, a liquid and a gas.

16. The method of claim 1, wherein the step of detection comprises a sensing mechanism selected from the group consisting of laser vibrometry, interferometry and measurement of photodopler shift.

17. The method of claim 1, wherein the step of detecting said vibration comprises:

directing a first portion of said SPOL through a beamsplitter, then into said area and onto said FM to produce first sensing light;

reflecting a second portion of said SPOL to a reflector and then into said area and onto said FM to produce second sensing light;
reflecting a portion of said SPOL to a detector;
interfering said first sensing light with said second sensing light to produce an interference pattern; and
analyzing said pattern with quadrature detection.

18. The method of claim 1, wherein the step of directing a SPOL comprises providing said SPOL through a fiber optic having an exit face operatively positioned with respect to said area, wherein the step of detecting said vibration comprises measuring Fabry Perot gap changes between said exit face and said FM.

19. The method of claim 1, wherein said FPOL and said SPOL are provided to said area through a single fiber.

20. The method of claim 1, wherein said FPOL and said SPOL are provided through separate fiber optics, wherein said separate fiber optics comprise a location selected from the group consisting of at about the same location and at different locations.

21. The method of claim 1, wherein said FPOL and said SPOL are provided on opposite sides of said FM.

22. The method of claim 1, wherein the step of detecting said vibration is selected from the group comprising detecting said vibration with a microphone and measuring resistance changes through piezoresistive traces on or in said FM.

23. The method of claim 1, wherein the step of detecting said vibration comprises measuring vibration of said FM through capacitive coupling.

24. The method of claim 1, further comprising substantially equalizing the power level of at least one of said FPOL and said SPOL.

25. The method of claim 1, wherein said area is divided into a first area and a second area, wherein said FPOL is directed onto said FM through said first area and said SPOL is directed onto said FM through said second area, wherein said first area comprises said MOI access port, wherein said second area comprises a known material for reference, wherein said known material does not absorb said FPOL.

26. The method of claim 9, wherein said MOMS sensor comprises a diameter selected from the group consisting of about 500 $\mu$m or less, about 2 mm or less and about 1 cm or less.

27. The method of claim 1, wherein said area comprises a long dimension selected from the group consisting of about 100 $\mu$m or less and about 20 $\mu$m or less.

28. A system for detecting a vibration of a flexible member, comprising:
a flexible member (FM) operatively fixed relative to an area such that a pressure change in said area will deflect said FM, wherein said area comprises a material of interest (MOI) access port;
means for directing a first pulse of light (FPOL) into said area during a first period of time (FPOT), wherein said FPOL comprises a wavelength $\lambda_1$ that is selected so that it will be absorbed by said MOI, if said MOI is located within said area, and produce first component of increased pressure within said area, wherein said FPOL produced component will produce a first deflection component of said FM, wherein if said FPOL heats a boundary of said area and produces a second component of increased pressure, said second component will produce a second deflection component of said FM;
means for preventing said FPOL from entering said area for a second period of time (SPOT);
means for directing a second pulse of light, (SPOL) onto said boundary during said SPOT, wherein said SPOL comprises a wavelength $\lambda_2$ that is selected so that it will heat said boundary to produce a third component of increased pressure within said area that is about equal to said second component of increased pressure, wherein during said SPOT, substantially only said MOI will cool, wherein said first deflection component will at least partially resolve by vibration of said FM; and
means for detecting said vibration.

29. The system of claim 28, wherein said FM comprises a reflective surface that is reflective to at least one wavelength of electromagnetic radiation (EMR).

30. The system of claim 28, wherein said FM is operatively fixed relative to an area by affixing said FM to said boundary such said FM is a between said area and an external area relative to said area.

31. The system of claim 28, wherein said FM is selected from the group consisting of a diaphragm and a cantilevered beam.

32. The system of claim 31, wherein said diaphragm comprises a diameter within a range from about 100 $\mu$m to about 425 $\mu$m.

33. The system of claim 31, wherein said FM comprises a thickness within a range from about 0.2 $\mu$m to about 0.5 $\mu$m.

34. The system of claim 28, wherein said FM comprises a flexible membrane.

35. The system of claim 28, wherein said FM comprises a micro-optical-mechanical system (MOMS) sensor is a microfabricated device.

36. The system of claim 35, wherein said MOMS sensor comprises a diameter of about 300 $\mu$m diameter and a thickness of about 2000 angstroms.

37. The system of claim 31, wherein said diaphragm is pre-buckled.

38. The system of claim 31, wherein said FM comprises a diameter and a thickness selected to controls the sensitivity of said FM to pressure.

39. The system of claim 28, wherein said area comprises a chamber having a long dimension selected from the group consisting of about 100 $\mu$m or less and about 20 $\mu$m or less.

40. The system of claim 29, wherein said area comprises a cylinder.

41. The system of claim 28, wherein said MOI is selected from the group consisting of a solid, a liquid and a gas.

42. The system of claim 28, wherein said means for directing a SPOL comprises a fiber optic having an exit face operatively positioned with respect to said area and further comprises means for measuring Fabry Perot gap changes between said exit face and said FM.

43. The system of claim 28, wherein said means for providing a FPOL and said means for providing a SPOL are selected from the group consisting of a single fiber, separate fiber optics, wherein said separate fiber optics comprise a location selected from the group consisting of at about the same location and at different locations, wherein said different locations are selected from the group consisting of the same side of said FM and opposite sides of said FM.

44. The system of claim 28, wherein said means for detecting said vibration comprise a microphone.

45. The system of claim 28, wherein said FM comprises piezoresistive traces on or in said FM, wherein said means for detecting said vibration comprise means for measuring resistance changes through said piezoresistive traces.

46. The system of claim 28, wherein said area is divided into a first area and a second area, wherein said means for directing said FPOL directs said FPOL onto said FM through said first area and said means for directing said SPOL directs said SPOL onto said FM through said second area, wherein said first area comprises said MOI access port, wherein said second area comprises a known material for reference, wherein said known material does not absorb said FPOL.

47. The system of claim 35, wherein said MOMS sensor comprises a diameter selected from the group consisting of about 500 μm or less, about 2 mm or less and about 1 cm or less.

* * * * *